United States Patent [19]

Takahashi et al.

[11] Patent Number: 5,124,082
[45] Date of Patent: Jun. 23, 1992

[54] METHOD FOR PREPARATION OF α, β-UNSATURATED CARBOXYLIC ACID CONTAINING FLUORINE

[75] Inventors: Mitsuru Takahashi, Shinnanyo; Hideo Shuyama, Hofo; Kiyotaka Oyama, Hikari, all of Japan

[73] Assignee: Tosoh Corporation, Yamaguchi, Japan

[21] Appl. No.: 71,831

[22] Filed: Jul. 10, 1987

[30] Foreign Application Priority Data

Jul. 11, 1986 [JP] Japan .................. 61-163359

[51] Int. Cl.$^5$ .................. C07C 51/15; C07C 57/52; C07C 57/54
[52] U.S. Cl. .................. 554/130; 562/550; 554/154; 554/155; 554/159; 554/223
[58] Field of Search ................ 562/550, 520; 260/408

[56] References Cited

U.S. PATENT DOCUMENTS 4,098,806  7/1978  Commeryas et al. .......... 260/408 X
4,578,222  3/1986  Ishikawa et al. .................. 260/413

Primary Examiner—Vivian Garner
Attorney, Agent, or Firm—Sughrue, Mion, Zinn, Macpeak & Seas

[57] ABSTRACT

A method for preparing α, β-unsaturated carboxylic acids of the formula $$R_1(R_2)C=C(R_3)CO_2H$$

where $R_1$ to $R_3$ can be hydrogen, fluorine, alkyl, or alkyl containing fluorine, but at least one of $R_1$ to $R_3$ is fluorine or alkyl containing fluorine. The method involves reacting an alkenyl halide containing fluorine having the general formula $$R_1(R_2)C=C(R_3)X$$

where $R_1$ to $R_3$ are the same as above, and X is chlorine, bromine, or iodine with carbon dioxide in an aprotic polar organic solvent and in the presence of activated zinc. The activated zinc is activated by pretreatment with a mineral acid or acetic acid. At least one cation is present during the reaction which is an alkali metal ion, alkaline earth metal ion or ammonium ion. The cation is present in an amount of 0.01 to 50 gram atoms per one mol of alkenyl halide containig fluorine. The resulting product is hydrolyzed.

7 Claims, No Drawings

METHOD FOR PREPARATION OF α, β-UNSATURATED CARBOXYLIC ACID CONTAINING FLUORINE

BACKGROUND OF THE INVENTION

1. Field of the Invention

The present invention relates to a method for preparation of α,β-unsaturated carboxylic acid containing fluorine, in detail, more particularly to a rapid and efficient method for producing α, β-unsaturated carboxylic acid containing fluorine starting from alkenyl halide containing fluorine as a raw material.

The α, β-unsaturated carboxylic acid containing fluorine is a useful substance as an intermediate raw material for various kinds of compounds containing fluorine, that is, a synthetic intermediate of pharmacological and agricultural medicaments, a material for paint, a raw material for polymers used in resists for the production of LSI, etc.

2. Description of the Related Art

Conventional methods for preparation of α, β-unsaturated carboxylic acid containing fluorine starting from an alkenyl halide as a starting material are as follows:

1) starting from vinyl bromide containing fluorine and n-butyl lithium or magnesium, vinyl lithium containing fluorine or magnesium bromide is prepared and reacted with carbon dioxide at lower temperatures ((J. Org. Chem.) 33, 280 (1967) or (Chem. Abs.) 53, 6987 g);

2) Vinyl halide compounds containing fluorine are reacted with carbon dioxide in the presence of a Zn - Cu pair (Japanese Patent Publication No. Sho 60-6332), or are irradiated with ultrasonic waves in the presence of zinc powder (10th Fluorine Chemistry Panel Discussion, 1985, p33);

3) in the presence of triethylamine and palladium catalyst, 2-bromo-3,3,3-trifluoropropene, carbon monoxide, and water are reacted to synthesize α-trifluoromethyl acrylic acid (Japanese Laid-Open Patent Applications No. Sho 58-154529, No. Sho 60-94933).

It is difficult to say, however, that these conventional methods are satisfied with adequate industrial technologies. That is, in the method using n-butyl lithium or magnesium, a reaction must be carried out at low temperatures such as $-100°$ C. or $-40°$ C. and the yield of objective products is also low.

In the method using a Zn - Cu pair there are some problems: a Zn - Cu pair must be prepared prior to a reaction, so that the procedure of reaction will become complicated, and it is difficult to prepare a Zn - Cu pair possessing a given activity, so reproducibility in yield cannot be observed, though sometimes relatively high yield can be obtained. Further, in the method wherein a reaction is carried out in the presence of zinc powder with irradiating ultrasonic waves, it is difficult to obtain a large size ultrasonic wave generating apparatus and yield is low. Therefore, from the point of industrial view it is difficult to say this method is an efficient one.

In the method using palladium catalyst, the catalyst is expensive and carbon monoxide has some problems on safety, hence it is hard to adopt this method as an industrial one.

In short, the conventional methods related to preparation of α,β-unsaturated carboxylic acid containing fluorine starting from the alkenyl halide containing fluorine have had some problems as follows:

1) conditions of reaction are severe,
2) yield is low, 3) the procedure of reaction is complicated.

SUMMARY OF THE INVENTION

From the aforesaid circumstances, intensive investigations were made by the present inventors to provide a method for preparing α,β-unsaturated carboxylic acid containing fluorine under a simple and mild condition with high yield.

Finally, in a method for reacting the alkenyl halide containing fluorine with carbon dioxide in the presence of zinc, the present inventors found that cations coexisting in the system of reaction made yield advance greatly and completed the present invention. The feature of the present invention is to react the alkenyl halide containing fluorine represented by general formula (I): $R_1(R_2)C=C(R_3)X$ (wherein $R_1$, $R_2$, and $R_3$ are hydrogen, fluorine, alkyl, or alkyl containing fluorine, and at least one is fluorine, or alkyl containing fluorine; X is chlorine, bromine, or iodine) with carbon dioxide in an organic solvent and in the presence of zinc and in coexistance of at least one sort of cation selected from alkali metal ions, alkaline earth metal ions, and ammonium ions in the system of reaction, and then to hydrolyze the reaction product to obtain α,β-unsaturated carboxylic acid containing fluorine represented by general formula (II): $R_1(R_2)C=C(R_3)CO_2H$.

Various alkenyl halides containing fluorine as represented by general formula (I) can be used in a method of the present invention and any one of $R_1$, $R_2$, and $R_3$ represented in general formula (I) should be fluorine or an alkyl group containing fluorine on the basis of reactivity of alkenyl halide and zinc. Examples of such compounds are vinyl halide compounds containing fluorine as represented by $F_2C=C(F)X$, $F_2C=C(H)X$, $H(F)C=C(F)X$, $H(F)C=C(H)X$, and $H_2C=C(F)X$ (wherein X is any of chlorine, bromine, or iodine), or 1- or 2-alkenyl halides containing fluorine, wherein hydrogen or fluorine of those compounds is substituted for alkyl or alkyl containing fluorine, as represented in $F_2C=C(R)X$, $F(R)C=C(F)X$, $H(R)C=C(F)X$, $F(R)C=C(H)X$, $H(F)C=C(R)X$, $F_2C=C(Rf)X$, $F(Rf)C=C(F)X$, $H(Rf)C=C(F)X$, $F(Rf)C=C(H)X$, $H(F)C=C(Rf)X$, $H_2C=C(Rf)X$, $R_2C=C(F)X$, $Rf_2C=C(F)X$, $Rf(F)C=C(F)X$, $Rf_2C=C(H)X$, $Rf(R)C=C(H)X$ (wherein R is an alkyl group; Rf is alkyl containing fluorine; X is any of chlorine, bromine, or iodine), and various substitution products of R and Rf as represented in $F(R)C=C(R)X$, $Rf(F)C=C(Rf)X$, $Rf_2C=C(Rf)X$, $Rf(R)C=C(R)X$, $R_2C=C(Rf)X$, $Rf_2C=C(R)X$, $Rf(R)C=C(Rf)X$, $R(F)C=C(Rf)X$, $Rf(F)C=C(R)X$, $Rf(H)C=C(Rf)X$, $Rf(H)C=C(R)X$, $R(H)C=C(Rf)X$ (wherein R is alkyl, Rf is alkyl containing fluorine, and X is any of chlorine, bromine, or iodine). In this case, taking into consideration the solubility of alkenyl halides containing fluorine to a solvent, the number of carbon atoms in the alkyl group or alkyl containing fluorine is preferably not more than 20. Further, any alkyl group containing fluorine possessing The effect of a substituent group similar to the trifluoromethyl group can be used, but a perfluoro or polyfluoro aliphatic group having a straight or branched chain is preferable.

In the method of present invention, at least one sort of cation selected from alkali metal ions, alkaline earth metal ions and ammonium ions should coexist in the reaction system.

In the present invention, an ammonium ion means $NH_4^+$ or one where all or a part of the hydrogen atoms in $NH_4^{30}$ are substituted by at least one sort of substituent selected from alkyl, aryl, or alkylene, or a cation wherein a substituent selected from hydrogen, alkyl, or aryl combines to a nitrogen atom of pyridine.

Examples of such cations are as follows:

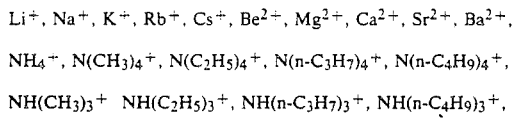

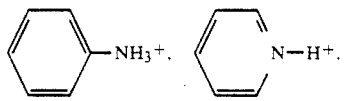

These cations can be applied to the present invention individually or in combination of several sorts. Furthermore, these cations can be easily supplied by addition of compounds consisting of these cations and anions to the system of reaction.

Examples of anions, not restricted especially, are as follows:

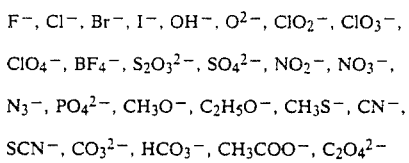

The amount of cations to coexist is preferably within the range from 0.01 to 50 gram atoms against 1 mol of alkenyl halide containing fluorine represented by general formula (I). The amount of cation less than 0.01 gram atom hardly has the effect of promoting yield and the amount more than 50 gram atoms results in having no effect of promoting yield in proportion to the amount of cation coexisting.

Zinc used in the method of the present invention may be employed in the form of powder, the mean size of particles in diameter preferably ranging from 0.1 to 100 μm. In the case that the particle is less than 0.1 μm in diameter, the procedure for removing it after the reaction will become complicated, and in the case that it is more than 100 μm in diameter, the yield of reaction will get small due to decrease in the effective area used during the reaction. Taking yield and procedure into consideration, the mean size of particles is preferably, in particular, 1 to 50 μm in diameter.

The amount of zinc can be decreased by pretreating the surface of zinc, though commercially available zinc powder can be utilized without treatment. The method for treatment of the surface is carried out according to the method of Houben-Weyl (Houben-Weyl), 13 (2a), 570 - 574, 815): pretreatment with acid treatment agents (mineral acids or acetic acid) and formation of metal pairs with other metals, e.g., in general, copper, lead, cadmium, mercury, etc.

Zinc powder may be used in the extent ranging from 1 to 10 equivalents against the alkenyl halide containing fluorine, preferably 2 to 10 equivalents to get a good reproducibility.

The preferable solvents in the method of the present invention are aprotic polar solvents, e.g. DMF, DMSO, N-N-dimethylacetamide, tetramethyl urea, hexamethylphosphoramide, sulfulane, N-methylpyrrolidone, nitrobenzene, nitromethane, acetonitrile, propylene carbonate, tetrahydrofurane, dioxan, ether, diglyme, triglyme, pyridine. From a yield point of view, the following are desirable: DMF, DMSO, N-methylpyrrolidone, N,N-dimethylacetamide, tetramethyl urea, and hexamethylphosphoramide.

The reaction in the present invention can be carried out within a wide extent of temperature, preferably 0° to 150° C. Since the temperature below 0° C. takes a long reaction time to promote conversion of the raw material, e.g. the alkenyl halide containing fluorine, it is not practical. The temperature above 150° C. lowers the objective selectivity coefficiency to carboxylic acid extremely, because of the increase in the ratio of side-reaction.

The reaction can be carried out by contacting the aforesaid alkenyl halide containing fluorine with carbon dioxide in the presence of cations in an organic solvent, and in a suspension of zinc at a given temperature. To supply carbon dioxide into the system of reaction, various ways can be adopted.

There are, for example, a way where carbon dioxide is introduced through a leading tube into the system and a way where carbon dioxide is forcefully dissolved in a solvent under pressure.

Taking yield into consideration, the alkenyl halide containing fluorine is desired to be added into the system at a given temperature in the presence of zinc, a solvent, carbon dioxide, and cations. It may be added by whole amount at one time, but another way can also be adopted wherein the raw material is introduced into the system at a constant rate. The rate is practically desired to be within the range from 0.01 to 10 mol/hr per 1 liter of solvent.

The time of reaction is adequate for 30 min to 100 hr after finishing addition of the alkenyl halide containing fluorine. However, in the case that the alkenyl halide containing fluorine is a solid and the aforesaid way cannot be adopted due to its small solubility in a solvent, the reaction can be carried out wherein the solvent is added to the system where zinc and halides have mixed with the compound containing cations in advance under an atmosphere of carbon dioxide. In this way, the time of reaction is adequate for 30 min to 100 hr after finishing addition of a solvent and setting at a given temperature.

As mentioned above, the objective compounds, $\alpha,\beta$-unsaturated carboxylic acids containing fluorine, can be obtained by hydrolysis of reaction products after reaction of the alkenyl halides containing fluorine with carbon dioxide in the presence of zinc and cations. Hydrolysis proceeds easily by contacting reaction mixtures with mineral acids such as hydrochloric acid, sulfuric acid, and nitric acid.

In the method of the present invention, the production of side-products is extremely depressed, so that alkenyl halides containing fluorine can be changed in high yield into the objective $\alpha,\beta$-unsaturated carboxylic acids.

Furthermore, the procedure for recovery of unreacted raw material gets useless and the processes for purification of the objective product get simple, which brings an effect of simplifying the procedure of isolation.

DETAILED DESCRIPTION OF THE PREFERRED EMBODIMENTS

The following Examples and Comparison Examples will illustrate the present invention in detail, but the present invention is not limitted thereto.

EXAMPLE 1

Into a 200 cc magnetic stirrer type autoclave, which is provided with an inlet port for carbon dioxide and an inlet port for 3,3,3-trifluoro-2-bromopropene, 7.85 g (0.12 gram atom) of zinc powder (mean particle of about 15 μm in diameter) which is washed with 0.2 N-HCl solution and dried in advance and 2.55 g (60 mmol) of lithium chloride were introduced and the temperature inside the autoclave was raised to 35° C. by heating. The pressure of carbon dioxide was 6.0 Kg/cm² pressure) through a constant pressure apparatus and until completion of the reaction the pressure inside the autoclave was continued.

Eighty ml of DMF was then introduced into the autoclave with stirring by the use of a transfer pump. DMF poured into the autoclave begins to dissolve carbon dioxide and the concentration finally shows the saturated dissolution concentration (1 mol/l) under a gaseous carbon dioxide pressure of 6.0 Kg/cm² (absolute pressure).

The mixture of 7.0 g (40 mmol) of 3,3,3,-trifluoro-2-bromopropene and 26 ml of DMF was then introduced into the autoclave by the use of a transfer pump over about ten min. After that, 10 ml of DMF was further introduced to wash the inside of the tube. After stirring for 24 hr at the same temperature, the pressure inside the autoclave was turned back to atmospheric pressure and the reaction was completed.

The gas-chromatographic result of the reaction solution showed 100 percent of conversion: 3,3,3-trifluoro-2-bromopropene as the raw material was all consumed.

After removing a solid from the reaction mixture by filtration, the filtrate was poured into 250 ml of N-HCl solution and the intermediate product was hydrolyzed. The extract with diethyl ether was then analyzed by gas-chromatography. The results showed that the objective α-trifluoromethyl acrylic acid was prepared in the yield of 79%.

EXAMPLES 2-9

The same procedure as Example 1, except that the compounds containing alkali metal ions as represented in Table 1 were used for lithium chloride as cations in 1.5-fold molar amount as much as 3,3,3-trifluoro-2-bromopropene, was carried out.

Results will be summarized in Table 1.

TABLE 1

| Example | Compounds Added | Conversion (%) | Yield (%) |
|---|---|---|---|
| 2 | NaI | 100 | 72 |
| 3 | KI | 87 | 75 |
| 4 | NaBr | 100 | 72 |
| 5 | KBr | 100 | 74 |
| 6 | NaCl | 100 | 71 |
| 7 | KCl | 100 | 72 |
| 8 | KF | 100 | 74 |
| 9 | CH₃COONa | 100 | 76 |

COMPARATIVE EXAMPLE 1

The same procedure as Example 1, except that lithium chloride was not used, was carried out.

The yield of α-trifluoromethyl acrylic acid prepared was 57%.

EXAMPLES 10-12

The same procedure as Example 1, except that the compounds containing alkali earth metal ions as represented in Table 2 were used for lithium chloride as cations in a 1.5-fold molar amount as much as 3,3,3-trifluoro-2-bromopropene, was carried out.

Results will be summarized in Table 2.

TABLE 2

| Example | Compounds Added | Conversion (%) | Yield (%) |
|---|---|---|---|
| 10 | MgCl₂ | 100 | 72 |
| 11 | BaCl₂ | 100 | 73 |
| 12 | MgBr₂ | 100 | 71 |

EXAMPLE 13

The same procedure as Example 1, except that the reaction temperature of 15° C. was used for 35° C. and the pressure of carbon dioxide of 11 Kg/cm² was used for 6 Kg/cm², was carried out. The yield of α-trifluoromethyl acrylic acid prepared was 92%.

EXAMPLE 14

The same procedure as Example 1, except for use of the atmospheric pressure for the pressure of carbon dioxide, was carried out. The yield of α-trifluoromethyl acrylic acid was 70%.

EXAMPLES 15, 16

The same procedure as Example 1, except that the compound containing ammonium ions as represented in Table 3 was used for lithium chloride as cations in a 1.5-fold molar amount as much as 3,3,3-trifluoro-2-bromopropene, was carried out.

Results will be summarized in Table 3.

TABLE 3

| Example | Compounds Added | Conversion (%) | Yield (%) |
|---|---|---|---|
| 15 | N(CH₃)₄Br | 100 | 70 |
| 16 | N(C₂H₅)₄I | 100 | 73 |

EXAMPLE 17

The same procedure as Example 1, except that the reaction time was 5 hr for 24 hr, was carried out.

3,3,3-trifluoro-2-bromopropene of the raw material was all consumed after the reaction, so that the conversion was shown to be 100%.

The yield of α-trifluoromethyl acrylic acid was 76%.

EXAMPLE 18

The same procedure as Example 1 was carried out, except that 8.9 g (40 mmol) of 3,3,3-trifluoro-2-iodopropene was used for 7.0 g (40 mmol) of 3,3,3-trifluoro-2-bromopropene.

The yield of α-trifluoromethyl acrylic acid obtained was 89%.

EXAMPLES 19-22

The same procedure as Example 1 was carried out, except that 3,3,3-trifluoro-2-bromopropene was replaced by 40 mmol of 3,3,4,4,5,5,6,6,6-nonafluoro-2-bromohexene, 1,2,2-trifluoro-1-iodoethene, 1,2-difluoro-1-iodo-3-methylpentene, or 2,3,3,4,4,5,5,6,6,7,7,8,8,9,9,9-hexadecafluoro-1-iodononene. The corresponding α,β-unsaturated carboxylic acids were prepared. The products were identified by IR, NMR, and so on.

Results will be indicated in Table 4.

TABLE 4

| Example | Product | Yield (%) |
|---------|---------|-----------|
| 19 | n-$C_4F_9C(CO_2H)=CH_2$ | 63 |
| 20 | $CF_2=CF.CO_2H$ | 91 |
| 21 | $CH_3CH_2CH(CH_3)CF=CH.CO_2H$ | 87 |
| 22 | n-$C_7F_{15}CF=CHCO_2H$ | 85 |

COMPARATIVE EXAMPLES 2-5

The same procedure as Examples 19-22, except that lithium chloride was not added, was carried out. Results will be summarized in Table 5.

TABLE 5

| Comparison Example | Products | Yield (%) |
|---------|---------|-----------|
| 2 | n-$C_4F_9C(CO_2H)=CH_2$ | 42 |
| 3 | $CF_2=CF.CO_2H$ | 79 |
| 4 | $CH_3CH_2CH(CH_3)CF=CF.CO_2H$ | 72 |
| 5 | n-$C_7F_{15}CF=CHCO_2H$ | 72 |

What is claimed is:

1. A method for preparation of α, β-unsaturated carboxylic acids having the general formula (I)

$$R_1(R_2)C=C(R_3)CO_2H \quad (I)$$

wherein $R_1$, $R_2$, and $R_3$ are hydrogen, fluorine, alkyl, or alkyl containing fluorine, and at least one thereof is fluorine or alkyl containing fluorine, which comprises:

(a) reacting an alkenyl halide containing fluorine having the general formula $$R_1(R_2)C=C(R_3) X$$

wherein $R_1$, $R_2$, and $R_3$ are same as the above definintion and X is chlorine, bromine, or iodine, with carbon dioxide in an aprotic polar organic solvent and in the presence of activated zinc, wherein the activated zinc is activated by pretreatment with a mineral acid or acetic acid, and at least one cation selected from the group consisting of alkali metal ions, alkaline earth metal ions, and ammonium ions, wherein the at least one cation is present in an amount of 0.01 to 50 gram atoms per 1 mole of alkenyl halide containing fluorine represented by general formula (I), and (b) hydrolyzing the resulting product.

2. A method according to claim 1, wherein the alkyl containing fluorine is a perfluoro or polyfluoro aliphatic group with a straight or branched chain of 1 to 20 carbon atoms.

3. A method according to claim 1, wherein the zinc is employed in an amount of 1 to 10 equivalents with respect to the alkenyl halide containing fluorine.

4. A method according to claim 1, wherein reaction is carried out at a temperature ranging from 0° to 150° C.

5. A method according to claim 1, wherein the alkyl or the alkyl containing fluorine of the alkenyl halide containing fluorine contains 20 or less carbon atoms.

6. A method according to claim 1, wherein the alkenyl halide containing fluorine is selected from the group consisting of 3,3,3-trifluoro-2-bromopropene, 3,3,4,4,5,5,6,6,6-nonafluoro-2-bromohexene, 1,2,2-trifluoro-1-iodoenthene, 1,2-difluoro-1-iodo-3-methylpentene, and 2,3,3,4,4,5,5,6,6,7,7,8,8,9,9,9-hexadecafluoro-1-iodononene.

7. A method according to claim 1, wherein the organic solvent is selected from the group consisting of dimethylformamide, dimethylsulfoxide, N-methylpyrrolidone, N,N-dimethylacetamide, tetramethyl urea, and hexamethylphosphoramide.

* * * * *